(12) United States Patent
Bowsher

(10) Patent No.: US 10,188,818 B2
(45) Date of Patent: Jan. 29, 2019

(54) RESPIRATORY MASK

(71) Applicant: INTERSURGICAL AG, Vaduz (LI)

(72) Inventor: Richard Francis Bowsher, Reading (GB)

(73) Assignee: Intersurgical AG, Vaduz (LI)

( * ) Notice: Subject to any disclaimer, the term of this patent is extended or adjusted under 35 U.S.C. 154(b) by 746 days.

(21) Appl. No.: 14/432,869

(22) PCT Filed: Oct. 3, 2013

(86) PCT No.: PCT/EP2013/070649
§ 371 (c)(1),
(2) Date: Apr. 1, 2015

(87) PCT Pub. No.: WO2014/053609
PCT Pub. Date: Apr. 10, 2014

(65) Prior Publication Data
US 2015/0250970 A1    Sep. 10, 2015

(30) Foreign Application Priority Data

Oct. 3, 2012   (GB) .................................... 1217713.5

(51) Int. Cl.
*A61M 16/06* (2006.01)
*A61M 16/08* (2006.01)
(Continued)

(52) U.S. Cl.
CPC ....... *A61M 16/0616* (2014.02); *A61B 5/0836* (2013.01); *A61B 5/097* (2013.01);
(Continued)

(58) Field of Classification Search
CPC .......... A61M 16/0616; A61M 16/0688; A61M 16/085; A61M 16/06; A61M 16/0683;
(Continued)

(56) References Cited

U.S. PATENT DOCUMENTS

| 2,625,155 A | 1/1953 | Engelder |
| 4,328,797 A * | 5/1982 | Rollins, III ........... A61M 16/06 |
| | | 128/202.15 |

(Continued)

FOREIGN PATENT DOCUMENTS

| CA | 2130732 A1 | 8/1993 |
| CA | 2130732 A1 | 2/1995 |

(Continued)

OTHER PUBLICATIONS

Capnoxygen LLC, "Capnoxygen™ mask FDA premarket notification summary", Sep. 23, 1997, available from the US Food and Drug Administration (FDA).

(Continued)

*Primary Examiner* — Gregory Anderson
*Assistant Examiner* — Jonathan Paciorek
(74) *Attorney, Agent, or Firm* — LeClairRyan PLLC

(57) ABSTRACT

A respiratory mask (10) for delivering inspiratory gas to a wearer, the mask comprising a mask body (12) shaped to define a cavity adapted to fit about the mouth and nose of the patient, wherein the mask body comprises a nose cavity portion (18) and a mouth cavity portion (16), the nose cavity portion comprising an inspiratory gas inlet port (26) and wherein the mouth portion comprises an expiratory gas monitoring port (34) at a location spaced from the inlet port. The gas monitoring port and may comprise an integral connector for a monitoring line and may be used to monitor carbon dioxide levels.

23 Claims, 2 Drawing Sheets

(51) Int. Cl.
*A61B 5/097* (2006.01)
*A61B 5/083* (2006.01)

(52) U.S. Cl.
CPC ........ *A61M 16/06* (2013.01); *A61M 16/0688* (2014.02); *A61M 16/085* (2014.02); *A61M 16/0683* (2013.01); *A61M 16/0816* (2013.01); *A61M 2202/0208* (2013.01); *A61M 2230/432* (2013.01)

(58) Field of Classification Search
CPC ........ A61M 16/0816; A61M 2230/432; A61B 5/0836; A61B 5/097
See application file for complete search history.

(56) References Cited

U.S. PATENT DOCUMENTS

| | | | | |
|---|---|---|---|---|
| 5,400,781 | A * | 3/1995 | Davenport | A61M 16/06 128/205.25 |
| 5,474,060 | A * | 12/1995 | Evans | A61B 5/097 128/204.22 |
| 6,273,087 | B1 * | 8/2001 | Boussignac | A61M 16/12 128/200.12 |
| 6,357,437 | B1 * | 3/2002 | Jacques | A61M 16/009 128/201.25 |
| 2003/0070675 | A1 | 4/2003 | McDonald | |
| 2005/0145247 | A1 * | 7/2005 | Nashed | A61M 16/00 128/204.18 |
| 2006/0032500 | A1 | 2/2006 | Ghiron et al. | |
| 2007/0101990 | A1 | 5/2007 | Hacke et al. | |
| 2007/0295335 | A1 | 12/2007 | Nashed | |
| 2009/0260628 | A1 * | 10/2009 | Flynn, Sr. | A61M 16/0078 128/203.28 |
| 2010/0263669 | A1 | 10/2010 | Bowsher | |
| 2011/0155136 | A1 | 6/2011 | Lee | |

FOREIGN PATENT DOCUMENTS

| | | |
|---|---|---|
| DE | 19831022 A1 | 7/1998 |
| EP | 1095269 B1 | 6/2004 |
| EP | 1582231 A1 | 10/2005 |
| JP | 03-254758 A | 11/1991 |
| WO | 9733641 A1 | 9/1997 |
| WO | 0209800 A1 | 2/2002 |
| WO | 2011/040219 A1 | 4/2011 |
| WO | 2012094730 A1 | 7/2012 |
| WO | 2013021172 A1 | 2/2013 |
| WO | 2013/036839 A1 | 3/2013 |

OTHER PUBLICATIONS

Fitzpatrick L., "The Correlation Between End-Tidal Carbon Dioxide Measured by Capnoxygen™ Mask and Nasal Cannula", Uniformed Services University of the Health Sciences, Oct. 2000, pp. 1-70.
Paul J., et al., "Both the OxyArm™ and Capnoxygen mask provide clinically useful capnographic monitoring capability in volunteers", Can J. Anesth, Feb. 2002, 50:2, pp. 137-142.
Great Britain Search Report for corresponding application GB 1217713.5 dated Apr. 15, 2013.
International Preliminary Report on Patentability for corresponding application No. PCT/EP2013/070649 dated Feb. 4, 2015.
International Search Report and Written Opinion for corresponding application No. PCT/EP2013/070649 dated Dec. 20, 2013.
UK Exam Report for Application No. GB1217713.5, dated Nov. 22, 2017, pp. 1-4.

* cited by examiner

RESPIRATORY MASK

This application is a national stage application under 35 U.S.C. § 371 of PCT International Application No. PCT/EP2013/070649, filed Oct. 3, 2013, which claims the benefit of Great Britain Application No. 1217713.5, filed on Oct. 3, 2012, which are hereby incorporated by reference in their entirety.

The present invention concerns a respiratory mask such as may be used in the therapy of a patient.

Respiratory masks are used to supply inhalation gases, and possibly also atomised liquids such as drugs in solution, to the airways of a patient. In general, a gas is supplied to a respiratory enclosure defined by the respiratory mask and the face of the patient, and the patient inhales the inhalation gas from this respiratory enclosure. Conventional masks typically also have an inlet for the inhalation gas, and an outlet through which exhaled gas escapes the respiratory mask.

UK Patent GB 2 412 594, in the name of Intersurgical Limited, discloses an example of such a respiratory mask. Masks of this type used in the therapy of patients can be distinguished from other breathing equipment which may be used by divers or members of the emergency services. Industrial breathing sets of that kind are generally complex and expensive and intended to provide a reusable source of breathable air to the user in inhospitable environments. In contrast, respiratory masks used for the therapy of patients, for example, within medical facilities are intended to be lightweight, typically disposable, articles merely for the delivery of gases to a patient, rather than protection from the environment.

Conventional respiratory masks for patient therapy typically comprise a unitary component defining a cavity and an outwardly-turned peripheral rim that is urged against the wearer's face, about their nose and mouth. The unitary component is typically a relatively thin-walled plastic structure, e.g. formed of polyvinylchloride (PVC), such that it provides a defined cavity shape, whilst offering a degree of flexibility to ensure a good fit against the wearer.

Furthermore conventional respiratory masks for patient therapy may be connected via tubing to a gas delivery unit and/or breathing circuit. It is known that within a breathing circuit an expiratory flow line may allow for a connection to a respiratory monitoring unit, which may be integral with a gas delivery unit, such as a ventilator or anaesthesia delivery machine. The expiratory flow line typically requires that a Y-piece connector and suitable valve arrangement is provided in order to provide a generally closed loop between the gas delivery unit and the patient. Some masks, such as oxygen masks, provide for an open-loop breathing circuit in which expiratory gas may escape through openings in the mask itself. Such masks are unsuitable for use with closed-loop circuits. However it is often desirous to be able to monitor one or more characteristics of expiratory gases in order to provide an indication of patient wellbeing.

US 2006/0032500 and U.S. Pat. No. 5,474,060 each disclose means for provision of a carbon dioxide monitoring fixture within the body of an oxygen mask. The provision of a dedicated monitoring line within the mask can increase the accuracy of measurement. However it has been found that the accuracy of carbon dioxide measurement can be variable. Also the inserts for the masks in the above-identified prior art increase the cost and complexity of manufacture of the mask.

It is an aim of the present invention to provide a respiratory mask, typically for patient therapy, which can offer an improved expiratory gas monitoring arrangement.

According to a first aspect of the invention, there is provided a respiratory mask for delivering inspiratory gas to a wearer, the mask comprising a mask body shaped to define a cavity adapted to fit about the mouth and nose of the patient, wherein the mask body comprises a nose cavity portion and a mouth cavity portion, the nose cavity portion comprising an inspiratory gas inlet port and wherein the mouth portion comprises an expiratory gas monitoring port at a location spaced from the inlet port.

The mask may be a patient therapy mask.

The inlet port may face a first direction (e.g. may be arranged about a first axis aligned with the first direction) and the gas monitoring port may face a second direction (e.g. may be arranged about a first axis aligned with the first direction).

The second direction may be angularly offset from the first direction. The first and second directions may be obliquely or perpendicularly arranged. The angle between the first and second directions may be greater than 45° or 60° and may be between approximately 60° or 70° and 90°.

The second direction may be angled such that the gas monitoring port in use faces generally between the nose and mouth of a wearer.

A mask having the gas monitoring port according to the present invention has been found to provide for accurate readings of the expiratory flow, for example carbon dioxide or other content thereof. In particular the port has been found to provide improved accuracy for low tidal volumes and/or may accommodate a patient breathing through the mouth or nose.

The mouth portion may comprise an upstanding wall arranged generally opposite the mouth of a wearer in use. The gas monitoring port may be located in the upstanding wall. The gas monitoring port may be located in the mask body in a region of intersection between an expiratory flow from a wearer's nose and an expiratory flow from a wearer's mouth.

In one embodiment, the gas monitoring port is offset from a longitudinal axis of the mask.

In one embodiment, the gas monitoring port comprises an upstanding port connector formation depending from the mask body. The connector formation may be integral with the mask body and may be formed therewith as a unitary member.

The connector formation may depend from an outer surface of the mouth cavity portion of the mask body. The connector formation may extend along the outer surface of the mask body. The gas monitoring port may be an inlet of the connector formation. The connector formation may comprise an outlet opening spaced from the gas monitoring port. The outlet may be angled, for example obliquely or substantially perpendicularly, to the gas monitoring port. An angle of between 45° and 90° may be suitable.

In one embodiment, the connector formation is generally tubular in form. The connector formation may comprise a gas monitoring tube or duct attached within the connector formation. The gas monitoring tube or duct may attach to the connector formation using an adhesive. An adhesive plug may be provided, for example within an opening in the connector formation and/or mouth portion of the mask body.

In one embodiment the mask and the gas monitoring duct may be formed of different materials. The adhesive may form a bond to a greater extent to one material than the other. The adhesive may solidify so as to form a plug or abutment feature between the duct and connector formation. The adhesive may bond to the duct material, thereby forming an abutment or plug in an opening/window of the mask body.

The inlet port in the nose portion may be arranged to direct gas away from the mouth portion. The nose portion may be arranged towards a first end of the mask body and the mouth portion may extend from the nose portion towards an opposing end of the mask body. The inlet port may be arranged to direct inhalation gas towards the first end. The nose portion may comprise an intervening wall depending outwardly from the mouth portion so as to define a nose cavity region of greater depth than that of the mouth region. The inlet port may be provided in the intervening wall.

The gas monitoring port may face the mouth of the wearer in use. The gas monitoring port may be provided at an upper region of the mouth portion, for example close to the region between mouth portion and nose portion (or intervening wall). The region of the mouth portion in which the gas monitoring port is provided may be obliquely angled relative to the nose portion.

The mask body may comprise a generally rigid polymer shell formed as a unitary piece and shaped to define the nose and mouth cavity portions, the monitoring ports extending through the shell between an interior and an exterior surface thereof.

The gas monitoring port may be, e.g. a carbon dioxide monitoring port, for delivery of gas to a monitoring machine.

According to a second aspect of the invention, there is provided a respiratory system comprising a mask according to the first aspect, a gas delivery unit for supplying gas via one or more ducts to the inlet port of the mask and a monitor for connection to the expiratory gas monitoring port for receiving a portion of the gas expired by the wearer in use.

Practicable embodiments of the invention are described in further detail below by way of example only with reference to the accompanying drawings, of which:

Figure 1:
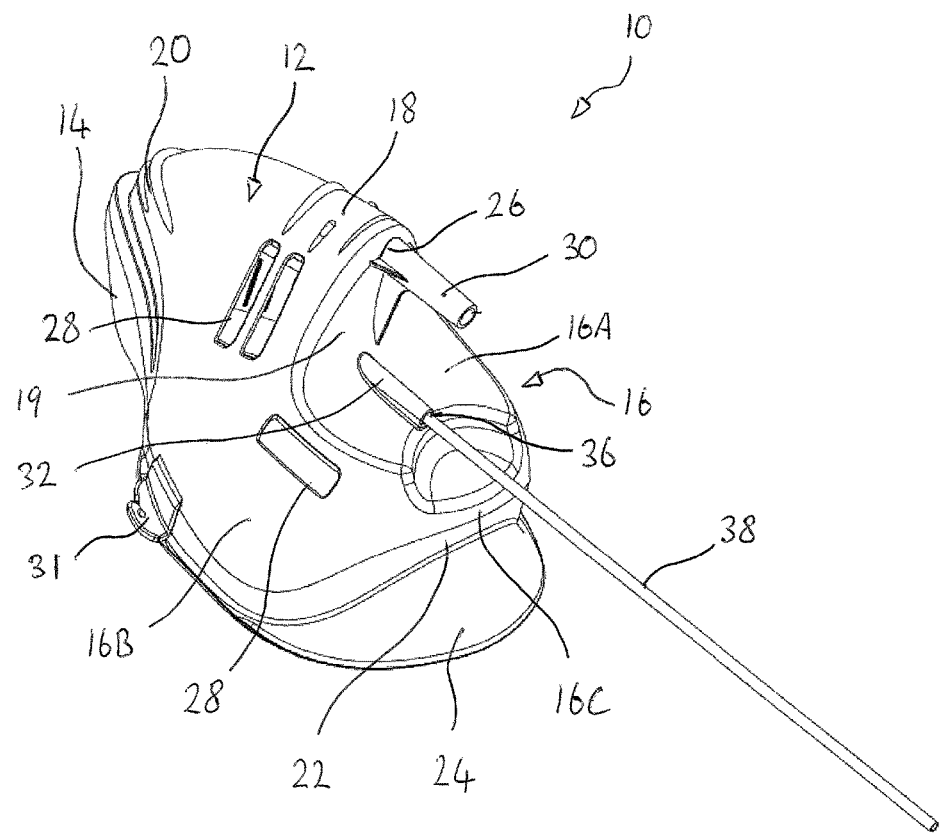
FIG. 1 shows a three-dimensional view of a respiratory mask according to an example of the invention.
Figure 2:
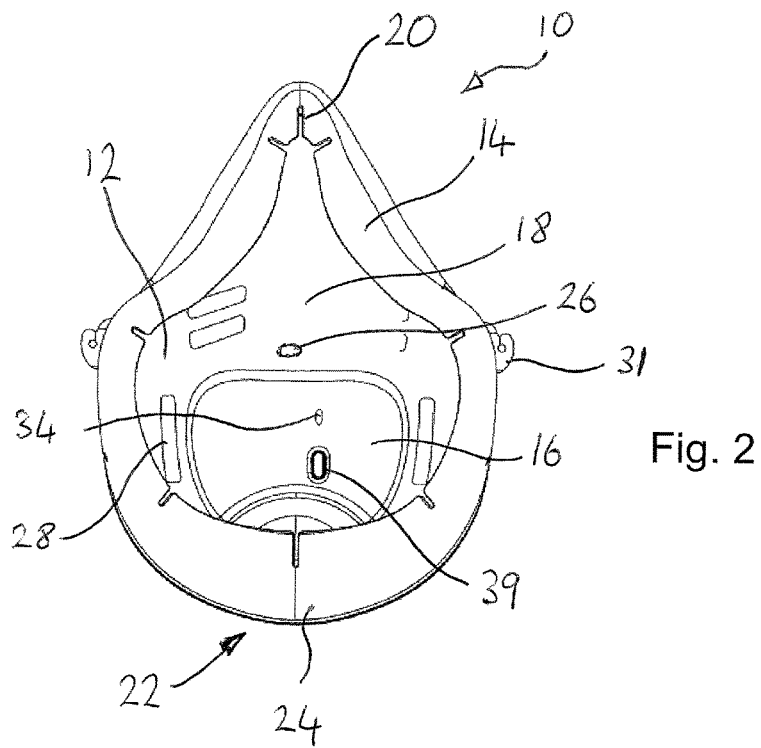
FIG. 2 shows a rear view of the mask of FIG. 1.

Turning firstly to FIGS. 1 and 2, there is shown a respiratory mask 10, which is suitable for the delivery of respiratory gases, such as oxygen, to a wearer, such as a patient. The respiratory mask comprises a mask body 12, formed from a suitably strong and relatively rigid plastics material, such as polypropylene or polyvinyl chloride, and a sealing formation 14 formed from a more flexible or complaint material, such as an elastomer. A Styrene-Ethylene-Butylene-Styrene (SEBS)-based thermoplastic elastomer may be used for the sealing formation. However it will be appreciated that other conventional mask body and seal materials may be used.

The respiratory mask is manufactured using a so-called two-shot injection moulding process. In particular, the mask body 12 is firstly injection moulded as a single component, and the sealing formation 14 is then injection moulded onto the surface of the mask body 10. The mask body 12 and the sealing formation 14 are bonded together by this process.

The mask body 12 is generally concave, so as to define a cavity via which an inhalation gas is delivered to a patient, and comprises a mouth portion 16 and a nose portion 18. The mask body is shaped such that the maximum depth of the cavity defined by the nose portion is greater than the depth of the cavity defined by the mouth portion. The nose portion 18 is generally tapered towards an apex 20 at a first end of the mask that is shaped to fit around the bridge of the patient's nose.

The mouth portion 16 generally comprises a forward-facing, front wall 16A and laterally-protruding side wall portions 16B, which are arranged to be located adjacent a wearer's cheeks or jowls, and particularly the lower portion thereof, in use. The mouth portion also comprises a lower wall or sill formation 16C beneath the front wall, i.e. at a second end of the mask 22, which is intended to contact with a wearer's chin.

An intermediate wall portion 19 is arranged between the mouth 16 and nose 18 portions of the mask body and effectively defines an interface between those portions. The intermediate wall is in the form of a shelf, for example which projects forwardly of the front wall 16A of the mouth portion. The intermediate or intervening wall 19 is angled, typically approximately perpendicularly to the front wall 16A. The intermediate wall defines a lower wall of the nose portion which projects beyond, or overhangs, the mouth portion.

The sealing formation 14 is a unitary flange member that is bonded to, and extends from, the peripheral edge of the mask body 12. The sealing formation 14 may pass substantially around the entire periphery of the mask body and may comprise an inwardly depending lip portion, which extends into the opening defined by the edge of the mask body. The sealing portion may have discontinuities therein in the form of slits which allow the seal to deform about the different contour portions of a wearer's face. In this example the sealing member also comprises a chin cup formation 24, which may provide a seal beneath the wearer's chin, particularly for wearer's having a larger facial length.

The elastomeric nature of the sealing formation 14 enables an effective seal to be formed between the contact surface of the respiratory mask and the face of the patient. However it will be appreciated that the mask may adopt different sealing formations about its peripheral edge in line with other conventional mask designs. Furthermore it is possible that the provision of a second, more-flexible sealing material 14 may be omitted altogether in the event that the seal quality is of little consequence to the mask provider.

The mask body 12 further comprises an inlet port 26 for connection to a supply of an inhalation gas, such as oxygen. The inlet port comprises an opening in the intermediate wall 19 (i.e. in a lower wall of the nose portion 18), and a tubular connector 30 that extends outwardly/downwardly away from the mask body into the space in front of the mouth portion 16. The free end of the connector 30 is thus disposed outside of the mask body in front of the mouth portion. In use, a supply of an inhalation gas is connected to the tubular connector of the inlet port 26 via a supply tube so as to supply the inhalation gas to the cavity of the respiratory mask and hence the airways of the patient.

The mask body has one or more exhalation openings 28, which may be spaced from the inlet opening 26. In this embodiment the exhalation openings are simple apertures in the wall of the mask body 10 that allow exhaled gases to exit the cavity of the respiratory mask. The exhalation openings may be elongate in form. A pair of exhalation openings is provided to either side of the nose portion 18. A generally vertically aligned exhalation opening is also provided on either side of the font face 16A of the mouth portion 16 (i.e. in side walls 16B). It will be appreciated that other shapes, configurations and orientations of exhalation openings are possible. In some embodiments, the exhalation openings may comprise a simple valve structure.

The body 12 has a pair of outwardly extending flange formations 31 on either side of the respiratory mask which are arranged to receive an elastic strap in use. Each flange is located adjacent the peripheral edge of the mask body and has an aperture, to which an elastic strap (not shown in the Figures) is attached, in use. The elastic strap extends between the flanges 31, and fits around the patient's head when the respiratory mask is fitted to the patient. In use, the strap is adjusted so that the respiratory mask is urged against the face of the patient with an appropriate force to ensure that an effective seal is formed between the periphery of the respiratory mask and the wearer's face, without causing excessive discomfort for the wearer.

Also shown in FIG. 1 is a monitoring line connector formation 32 located on the front wall 16A of the mouth portion 16. The connector formation 32 is integrally formed with the mask body 12, for example comprising the same material as the mask body such that the connector formation 32 is a unitary member with the mouth portion 16 of the mask body. The connector formation may be formed in a single moulding shot or process with the remainder of the mask body.

The connector 32 comprises a generally tubular formation having an opening or port at either end thereof. The connector 32 runs from a first port 34 (see FIG. 2) which provides an opening into the interior of the mask body cavity to a second port or outlet opening 36 (see FIG. 1) which provides an open ended connector formation arranged to receive a monitoring line 38. The monitoring line may be a conventional PVC duct or other suitable material.

The connector formation 32 runs along the exterior of the front wall 16A of the mouth portion 16 in a downward direction, i.e. away from the nose portion or towards the second end 24 of the mask. The connector formation may be substantially parallel with the inlet connector formation 30 but spaced therefrom. This has the benefit that the monitoring line connector 32 provides a sturdy connector with minimal protrusion and is not prone to being caught or else impeding normal operation of the mask. Furthermore it is advantageous that the monitoring line 38 extends in substantially the same direction as an inlet line (not shown) connected to the inlet connector 30 in use. The lines can thus be easily managed.

In the embodiment shown, the monitoring line connector 32 is slightly offset laterally from the central axis of the mask and/or inlet connector. This offset simplifies the tooling for the product during manufacture. However in other embodiments the connector formation may be otherwise be located in the mouth portion such that the monitoring port 34 can achieve one or more of the benefits to be described below. For example the port 34 may be moved to alternative locations within the front wall 16A or side walls 16B.

The monitoring line 38 is generally tubular and arranged to be received within the formation 32 such that the end of the monitoring line passes part way along its tubular interior. The monitoring line may be formed of a conventional polymer material, such as PVC or the like.

In this example, the monitoring line is held within the formation 32 by way of an adhesive (e.g. a glue). A conventional adhesive, such as an ultra-violet activated glue, suitable for fixing plastic components for medical applications, may be used. In the present embodiment, the connector formation 32 has an opening or window 39 part way along its length, i.e. spaced from the port 34 and open end of the formation. The opening or window 39 is provided in a side wall portion of the connector formation and may be provided through the wall of the mask body such that the opening is accessible from the interior of the mask as shown in FIG. 2. Alternatively the opening could be provided on the exterior surface of the formation 32 such that it is accessible from outside the mask.

The opening 39 is particularly beneficial in that it allows an end of the monitoring line 38 to be inserted into the connector formation beyond the location of the opening 39 (e.g. such that the end of the monitoring line 38 terminates between the port 34 and opening 39. Adhesive can be applied via the opening such that the monitoring line is held fast within the formation 32. An adhesive plug may be provided in this manner into/via the opening 39 which does not therefore interfere with the end of the monitoring line 38 and thus does not present a potential blockage to flow into the monitoring line. An end stop or similar formation may be provided in the connector formation 32 to aid correct location of the monitoring line therein prior to application of the adhesive.

Additionally or alternatively it has been found that the opening provides a 'well' formation or recess into which the adhesive can be reliably applied. In addition to providing an adhesive application site, the opening also provides a mechanical keying site or abutment against which the solidified adhesive may be held in use. That is to say the adhesive may solidify to form a plug member in the opening which resists removal of the monitoring line 38 in use. Such a plug provides a mechanical abutment which resists unwanted removal of the monitoring line in use in addition to the chemical bond with the adhesive. This has been found to be particularly important for adhesives which bond well to the monitoring line but less well to the mask body (e.g. to polypropylene or similar, generally rigid, polymer materials). Thus the arrangement resists removal from the mask, for example due to unintentional pulling on the monitoring line even if the adhesive has achieved only a weak bond between the mask body and monitoring line.

Figure 3:
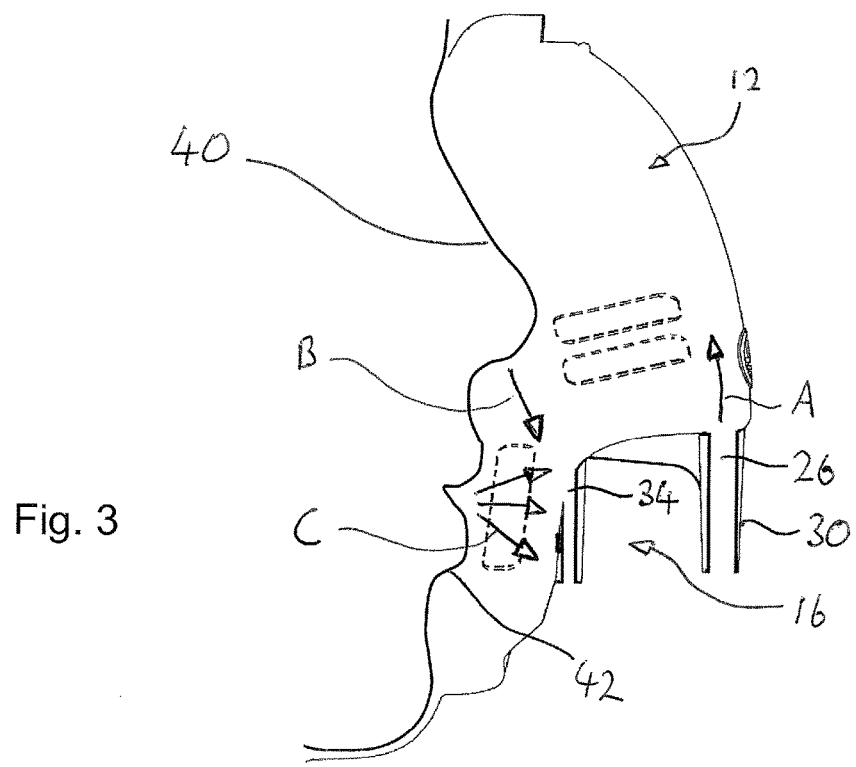
FIG. 3 shows a sectional view through the mask of FIG. 1 in use.

Turning now to FIG. 3, there is shown an example of the mask in use, wherein the mask is urged against a wearer's face such that the first end 20 is uppermost and rests against the bridge of the wearer's nose 40, typically at, or slightly below, the nasion. The second end 24 is located beneath the wearer's mouth 42, typically in the vicinity of the chin.

The wearer's nose 40 and mouth 42 are located in the mask cavity. The wearer's mouth is accommodated within the mouth portion 16 of the mask body 12 and the wearer's nose is accommodated within the nose portion 12. The nose portion 12 is tapered towards the upper end of the mask and hence the bridge of the patient's nose.

The expiratory monitoring port may be substantially in front of, or diametrically opposite, the wearer's mouth.

In use, gas is supplied to the mask interior in the direction A via the inlet 26, thereby generally flooding the nose portion 12 at least. During inspiration, gas within the interior of the mask is drawn in via the nose and/or mouth. In the event that the rate at which gas is drawn into the wearer's lungs is greater the gas supply rate via the inlet 26, additional ambient air will be drawn into the mask via openings 28.

During expiration, the wearer may breathe out via either their nose or mouth in the direction of arrows B or C. The monitoring port 34 in the above-described location has been found to be particularly beneficial since it is arranged generally at the intersection between the expiratory flows from the mouth and nose. Accordingly the expired flow impacts directly the mask body in the vicinity of the monitoring port 34 in a consistent manner. The port 34 thus receives a portion of the fastest flowing gas in the expiratory flow.

Furthermore, since only a portion of the expiratory flow will pass immediately through the port, once the expiratory flow has impacted the interior surface of the front wall 16A, it will tend to fill the lower/mouth portion of the mask in the vicinity of the opening 34, such that any further flow through port 34 and along monitoring line 38 will contain a relatively consistent and accurate reflection of the true expiratory flow.

This arrangement is beneficial over the provision of an expiratory monitoring line within the intermediate wall 19 of the nose portion. Such a location of expiratory monitoring port is typically preferred in order to provide a connector close to the inlet connector and also in the belief that providing a monitoring port close to the wearer's nose provides for accurate readings of expired gas. However the inventor has determined that the flow of gas into the mask in the direction of arrow A as shown in FIG. 3 can flood the nose portion of the mask and that the expiratory flow can establish a regime wherein the monitoring port is at least partially bypassed by the expiratory flow, or else that the expiratory flow mixes with incoming gas prior to passing through the monitoring port. Furthermore the inventor has determined that this problem is exacerbated if the patient breathes through their mouth since the incoming gas flow and the expired gas flow meet prior to passage along the monitoring line in such as way as to promote mixing or else establish a recirculation of incoming gas within the nose portion of the mask.

Accordingly the invention has been found to improve the accuracy of the monitoring of expiratory gas flow, whilst also providing for a particularly cost effective mask construction. Furthermore the invention avoids the need for a monitoring port projection on the interior of the mask in order to locate the port close to the wearer's nose. The invention thus allows an expiratory gas monitoring capability to be implemented with minimal additional cost or weight to the mask and minimal disruption to the operator or wearer.

Also the invention allows a monitoring connector formation to be formed with the mask body such that it cannot be inadvertently disconnected or lost during use.

The monitoring line typically passes to a suitable monitoring means, which, in the example of carbon dioxide monitoring, may comprise a capnograph. The monitoring line maybe removably connected to the monitor by a suitable connector, such as for example a luer connector. Whilst the mask is primarily intended to allow for carbon dioxide monitoring for an oxygen delivery mask, it is not limited thereto and may be used to monitor other gas concentrations within the expired flow and/or other parameters, such as flow rate, pressure or similar.

Whilst the above description refers to a mask type typically used for supply of oxygen to a patient, the invention may also be applied to other patient therapy mask types, such as an aerosol mask. In other embodiments, a reservoir bag of conventional type may be provided in communication with the mask inlet so as to provide a so-called high-concentration mask.

The invention claimed is:

1. A respiratory mask for delivering inspiratory gas to a wearer, the mask comprising a mask body shaped to define a cavity adapted to fit about the mouth and nose of the patient, wherein the mask body comprises a nose cavity portion and a mouth cavity portion, the mask body being shaped such that the maximum depth of the cavity defined by the nose portion is greater than the depth of the cavity defined by the mouth portion, the nose cavity portion comprising an inspiratory gas inlet port and the mouth cavity portion comprising an expiratory gas monitoring port, at a location spaced from the inlet port, wherein the gas monitoring port is an inlet of a port connector formation depending from the mask body, and wherein said port connector formation is integral with the mask body.

2. The respiratory mask according to claim 1 wherein the inlet port faces a first direction and the gas monitoring port faces a second direction, which is angularly offset from the first direction.

3. The respiratory mask according to claim 2, where in the angle between the first and second directions is greater than 45°.

4. The respiratory mask according to claim 1 wherein the mouth portion comprises a front wall arranged generally opposite the mouth of a wearer in use and the gas monitoring port is located in the front wall.

5. The respiratory mask according to claim 1, wherein the gas monitoring port is offset from a longitudinal axis of the respiratory mask.

6. The respiratory mask according to claim 1, wherein the gas monitoring port is located in the mask body in a region of intersection between an expiratory flow from a wearer's nose and an expiratory flow from a wearer's mouth.

7. The respiratory mask according to claim 1, wherein mask body and connector formation are moulded as a unitary member.

8. The respiratory mask according to claim 1, wherein the connector formation extends along an outer surface of the mask body and comprises an outlet opening spaced from the gas monitoring port.

9. The respiratory mask according to claim 8, wherein the outlet is substantially perpendicular in orientation to the gas monitoring port.

10. The respiratory mask according to claim 1, wherein the connector formation is generally tubular in form.

11. The respiratory mask according to claim 1, comprising a gas monitoring tube or duct attached within the connector formation.

12. The respiratory mask according to claim 1, comprising a gas monitoring tube or duct attached to the connector formation using an adhesive, wherein the connector formation comprises a window in a side wall thereof through which the adhesive is applied.

13. The respiratory mask according to claim 12, wherein the window provides a keying or abutment site and the solidified adhesive forms an abutment feature within the window.

14. The respiratory mask according to claim 1, wherein the inlet port in the nose portion is arranged to direct gas away from the mouth portion.

15. The respiratory mask according to claim 1, wherein the nose portion comprises a first end of the mask body and the mouth portion comprises an opposing end of the mask body, wherein the inlet port is arranged to direct inhalation gas towards the first end.

16. The respiratory mask according to claim 1, wherein the nose portion comprises an intervening wall depending outwardly from the mouth portion so as to define a nose cavity region of greater depth than that of the mouth region, wherein the inlet port is provided in the intervening wall.

17. The respiratory mask according to claim 1, wherein the gas monitoring port faces the mouth of the wearer in use.

18. The respiratory mask according to claim 1, wherein the mask body comprises a generally rigid polymer shell formed as a unitary piece and shaped to define the nose and mouth cavity portions, the ports extending through the shell between an interior and an exterior surface thereof.

19. The respiratory mask according to claim 18 wherein the mask body has a peripheral edge, the mask further comprising a softer seal material bonded onto the peripheral edge and arranged to form a seal with a wearer's face in use.

20. The respiratory mask according to claim 1, wherein the gas monitoring port is a carbon dioxide monitoring port for delivery of gas to a monitoring machine.

21. The respiratory mask according to claim 1, wherein the mask body comprises one or more outlet openings allowing expiratory flow to exit the mask to the surrounding air.

22. A respiratory system comprising the respiratory mask according to claim 1, a gas delivery unit for supplying gas via one or more ducts to the inlet port of the mask and a monitor for connection to the expiratory gas monitoring port for receiving a portion of the gas expired by the wearer in use.

23. The use of the respiratory mask according to claim 1 for monitoring carbon dioxide content in the expiratory flow of a wearer.

\* \* \* \* \*